United States Patent [19]

Kimonides

[11] Patent Number: 4,790,197

[45] Date of Patent: Dec. 13, 1988

[54] LIQUID SAMPLING APPARATUS

[76] Inventor: Riginos Kimonides, 18 Chatsworth Road, Stamford, Lincolnshire PE9 2UM, England

[21] Appl. No.: 79,104

[22] Filed: Jul. 29, 1987

[51] Int. Cl.[4] .............................................. G01N 1/12
[52] U.S. Cl. .................................................. 73/864.65
[58] Field of Search ........... 73/864.65, 864.64, 864.66, 73/864.67, 864.63, 864.61, 864.62

[56] References Cited

U.S. PATENT DOCUMENTS

| 540,121 | 5/1985 | Tagliabue | 73/864.65 |
|---|---|---|---|
| 1,621,857 | 3/1927 | Seraphin | 73/864.65 |
| 2,071,145 | 2/1937 | Summers | 73/864.65 |
| 2,155,601 | 4/1939 | Johnson | 73/864.65 |
| 2,166,779 | 7/1939 | Arntzen | 73/864.65 |
| 2,192,065 | 2/1940 | Sandstone | 73/864.65 |
| 2,607,229 | 8/1952 | Quist | 73/864.65 |
| 2,713,269 | 7/1955 | Neer | 73/864.65 |
| 3,680,389 | 8/1972 | Binkley, Jr. et al. | 73/864.65 |

FOREIGN PATENT DOCUMENTS

| 352600 | 5/1922 | Fed. Rep. of Germany | 73/864.65 |
|---|---|---|---|
| 330317 | 6/1930 | United Kingdom | |
| 566752 | 1/1945 | United Kingdom | |
| 2072145 | 9/1981 | United Kingdom | |

Primary Examiner—Stewart J. Levy
Assistant Examiner—Robert R. Raevis
Attorney, Agent, or Firm—Henry Sternberg; Bert J. Lewen

[57] ABSTRACT

Liquid sampling apparatus for sampling liquid at a controlled depth within the tanks of an ocean going oil tanker comprises a sampling chamber having outwardly opening inlet and outlet valves. The inlet valve 114 is arranged to be actuated by a projecting valve actuator 132 through a lever mechanism and is adjustable by means of a spring clip 136 so as to permit sampling at varying distances from the bottom of the tank. The outlet valve is a pressure-relieving ball valve 138 permitting automatic escape of air during filling of the sampling chamber, but preventing entry of liquid. The apparatus is lowered in use through an MMC stand on a wire carried by a support 140 at the top of the apparatus.

7 Claims, 4 Drawing Sheets

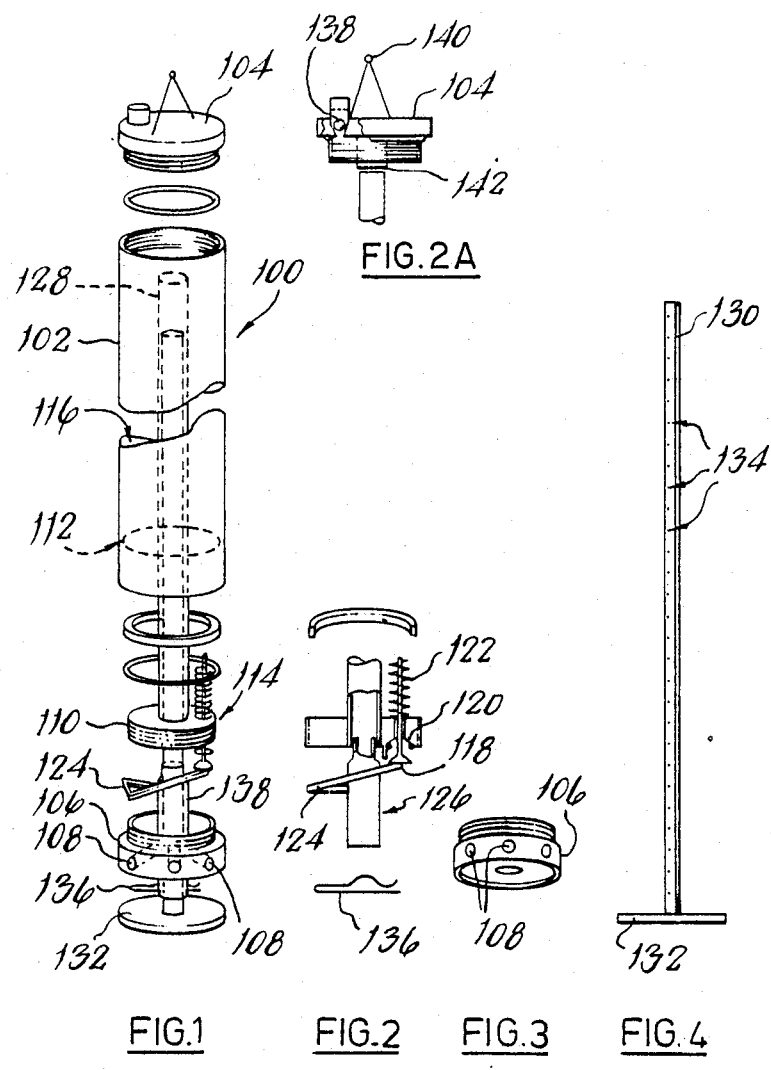

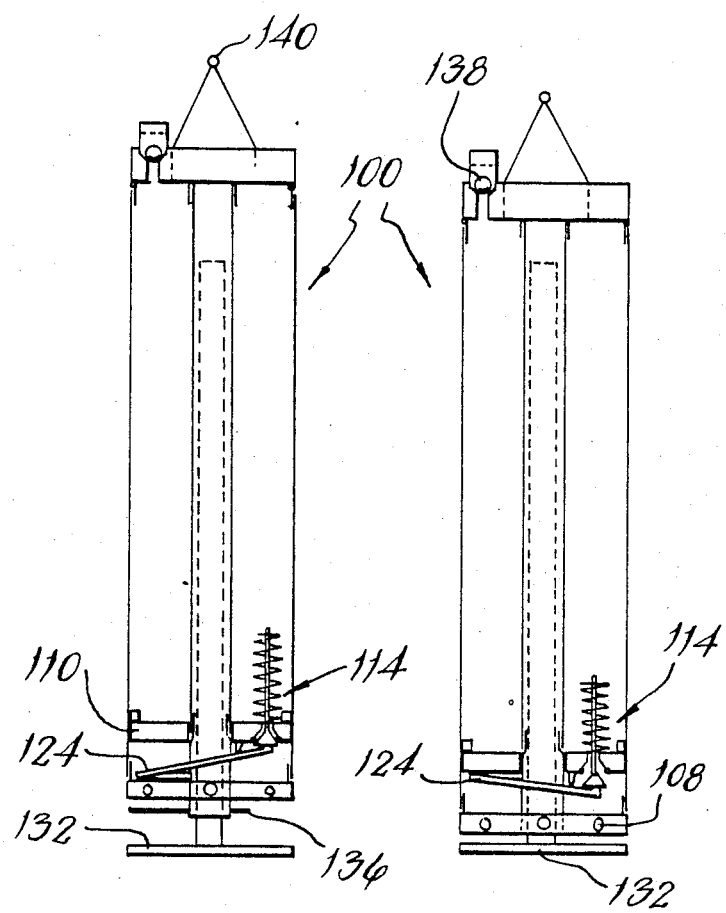

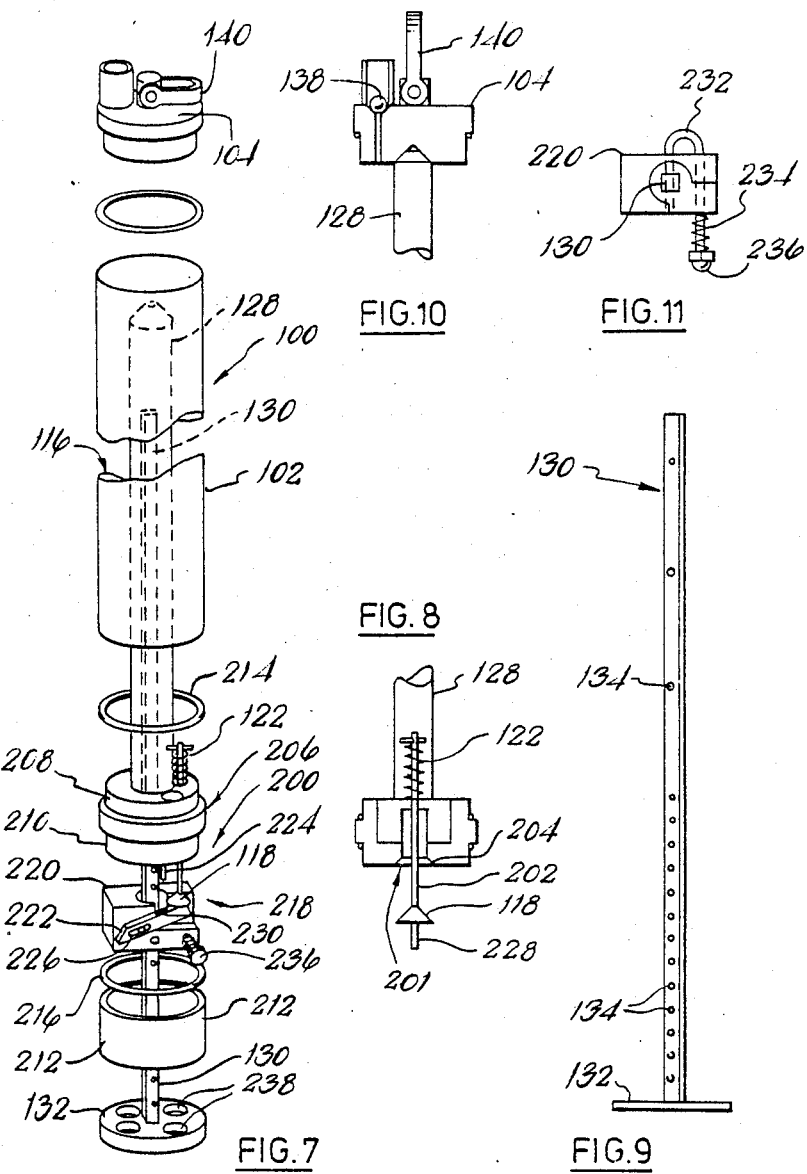

LIQUID SAMPLING APPARATUS

BACKGROUND OF THE INVENTION

This invention relates to liquid sampling apparatus. There is disclosed below such apparatus for obtaining samples of water from a mixture of oil and water contained in oil tanks, especially the tanks of ocean going oil tankers, corresponding shore tanks, and underground fuel storage tanks, where access to the base of the tank is difficult to obtain. The invention is also applicable to other liquid sampling environments, including sampling from storage tanks and vats generally, the sea bed, rivers and other waterways, reservoirs and wells, and analogous applications.

There is a need to obtain water samples from the water which is often found to be mixed with the oil in the tanks of oil tankers. Such water samples are used for analysis purposes. The analysis enables data to be obtained which may permit identification of the source of the water.

There is disclosed in U.S. Pat. No. 3,680,389 (Binkley) sampling apparatus for a waste disposal system, particularly for use at an off-shore location. A sampling vessel has upper and lower valves actuated by a projecting foot. The foot is connected by an actuating rod 43 to the two valves to actuate same, and thus they both open upwards. Coiled compression springs 56,57 hold the valves in their closed position. An annulus 33 is provided to house heavy ballast material whereby the weight of the apparatus can be sufficient to enable the valves to be opened through the medium of foot 58 and rod 43.

There is a need for improvements with respect to the above-mentioned prior art in several respects. Firstly, there is a requirement for sampling apparatus which is smaller and lighter in weight and thus easier to handle than the prior art. In particular, it would be beneficial if the need for ballast weight could be avoided. Secondly, with regard to the application of the sampling apparatus to situations in which it is desired to sample liquid at a well defined depth, and perhaps varying depths, close to but not necessarily at the bottom of an oil tank, or on the sea bed, there is a need for means whereby this can be achieved. Other desirable refinements relate to the general construction of such a device, its economy of manufacture and ease of use.

Accordingly, a general aim of the invention is to provide liquid sampling apparatus having improved means for operating the valves thereof, particularly means whereby the load required to open the valves is reduced.

Another aim of the invention is to provide liquid sampling apparatus having means whereby the depth at which the valves are opened, can be adjusted.

Still another aim of the invention is to provide liquid sampling apparatus which can be made in a form which is lighter in weight, less bulky, and more readily utilised.

SUMMARY OF THE INVENTION

The present invention resides in liquid sampling apparatus having a sealable sampling vessel defining a chamber to receive and temporarily store a liquid to be sampled. Upper and lower ports are formed in the sampling vessel to permit escape of air and entry of liquid to be sampled, during the sampling process. Upper and lower valve means are mounted at the ports to control the passage of fluids through the ports. According to one feature of the invention, both the upper and lower valve means comprise valve members mounted for movement outwards and inwards with respect to the sampling vessel, respectively to open and close the valves.

In accordance with another feature of the invention, the lower valve means is actuatable by a projecting actuator member which is engageable with a bottom surface of a liquid tank or the like being sampled. The actuator member is connected to the valve member by a lever mechanism whereby inward movement of the actuator member causes outward movement of the valve member.

In the embodiments, by the provision of outwardly opening valve members, the need for substantial valve closure springs is avoided. The liquid pressure itself tends to hold the valves shut. Therefore, a relatively small actuating thrust is capable of opening at least the lower liquid inlet valve. In this way, the weight of the apparatus when constructed from conventional materials is usually sufficient for the purpose.

In the embodiment also, the upper valve means, for air escape, is constructed as a ball valve which opens as a result of increasing air pressure within the chamber. In this way, the need for direct actuation of the upper valve is avoided.

A further feature of the embodiment lies in the provision of adjustable connecting means between an extensible actuator projecting from the base of the apparatus, and the valve operating mechanism, whereby the apparatus can be set to commence sampling at varying distances from the bottom of an oil tank or the like.

BRIEF DESCRIPTION OF THE FIGURES

FIGS. 1, 2, 2A, 3, and 4 show in generally exploded form, liquid sampling apparatus according to the invention;

FIGS. 5 and 6 show sectional views through the assembled apparatus of FIGS. 1 to 4 in its valve-closed and valve-open configurations; and FIGS. 7 to 13 show a second embodiment, the views corresponding, generally speaking, to those of FIGS. 1 to 6;

FIG. 7 shows an exploded view of the apparatus corresponding to FIG. 1;

FIG. 8 shows a scrap sectional view showing details of an inlet valve arrangement;

FIG. 9 shows a valve actuating rod;

FIG. 10 shows a scrap sectional view of an outlet valve assembly;

FIG. 11 shows a detail of a finger-actuated adjustment mechanism for the rod of FIG. 9;

FIGS. 12 and 13 show the assembly of FIG. 7 with the inlet valve in its closed and open positions respectively.

DETAILED DESCRIPTION

Figure 12:
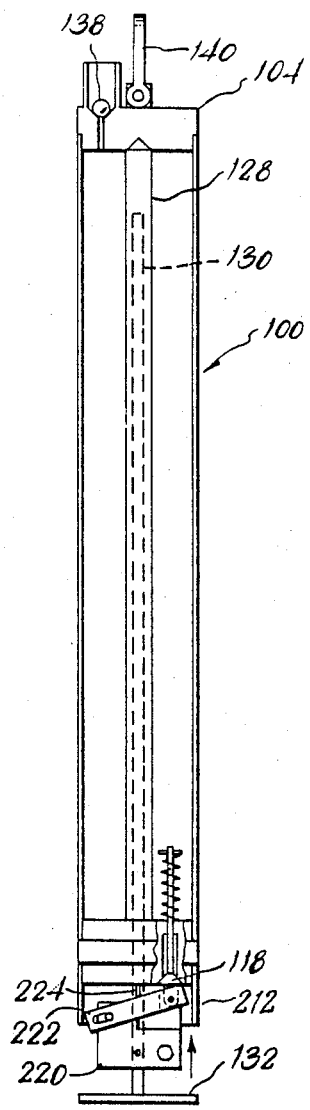

As shown in the drawings, liquid sampling apparatus 100 comprises a sealable sampling vessel having a main tube 102 with a top cap 104 and a bottom cap 106, the latter being formed with radial drillings 108 forming screening inlet openings leading to the interior of tube 102. A collar 110 fits within tube 102 and seats against an internal shoulder 112 formed therein. Between collar 110 and top cap 104 there is defined a chamber to receive and temporarily store a liquid to be sampled.

A lower valve assembly 114 controls the inlet of liquid from openings 108 through a port in collar 110 into the sampling chamber 116 above the collar.

Lower valve assembly 114 comprises a sliding valve member 118 adapted to seat against a conical valve seat 120 formed in collar 110 and biased by a valve spring 122, to its closed condition shown in FIG. 5. The lower end of valve member 118 is actuated by a lever-type valve actuating arm 124 which is pivotally mounted on a central valve actuating assembly 126 slidably mounted in a guide tube 128 within main tube 102.

The valve actuating assembly includes a central rod 130 having a base plate 132 and formed with apertures 134 whereby the rod is adjustably connected by means of a spring clip 136 to a tube 138. In this way, base plate 132 is mounted at an adjustable distance from the valve actuating lever 124 for a purpose to be described.

At the top of the apparatus a ball-type non-return valve 138 operates as a pressure-relief valve, permitting air to escape during sampling through a port formed in top cap 104, but preventing water (or other liquids) entering.

The drawings also show O-rings and other sealing members forming part of the apparatus, as will be appreciated by those skilled in the art.

In use, base plate 132 is set at the desired distance below bottom cap 106 so as to cause inlet apertures 108 to sample the liquid at the desired height above the base of the tank. The apparatus is lowered into the liquid to be sampled with the main tube 102 full of air. The weight of the apparatus causes same to descend through the liquid. Ball valve 138 prevents the entry of liquid. At this stage, valve spring 122 is holding lower valve 114 in its closed condition. When the apparatus reaches the base of the tank, or the sea bed, the weight of the apparatus causes an upthrust to be applied to the valve actuating members thereby pivoting lever 124 and causing valve 114 to open, as shown in FIG. 6, this permits liquid to enter tube 102. The rise in air pressure unseats ball valve 138 and allows the air in the chamber to escape. After a certain time interval the chamber is full and the apparatus can be raised on the lift gear 140.

It will be noted that an end tube 142 in top cap 104 receives guide tube 128, thereby supporting same against bending stress during use.

Further features to which attention is directed in the embodiment include the relatively small diameter of the liquid entry valve 114 as compared with the diameter of the chamber 116, whereby the thrust due to liquid pressure at the sampling depth, exerted on valve member 118 is proportionately reduced, so that spring 122 can be correspondingly light in action. Preferably, the external diameter of the valve member 118 is less than half the diameter of the chamber, and preferably about a quarter, or less.

In the embodiment, main tube 102 is formed of brass and thus has fully adequate weight to actuate valve 114 at all normal operating depths of the apparatus.

The moving parts of the apparatus are preferably manufactured of stainless steel. The inlet drillings 108 act as a screen or filter device. In use, a period of the order of sixty seconds may be required to allow the apparatus to fill with the liquid being sampled. During this period, air within the apparatus escapes through valve 138. This latter valve permits easy emptying of the liquid sample after use. For this latter purpose, valve 114 should preferably be manually held in its open position by pushing inwards on foot 132.

In the embodiment, the above-described valve arrangements avoid the disadvantages of certain prior art apparatus that there was a tendency for liquid to enter the sampling chamber before the required sampling depth had been attained, thereby negating the entire purpose of the sampling exercise.

In the embodiment shown in the drawings the maximum variation in sampling depth corresponds, more or less, to the axial length of the apparatus. However, by means of a simple modification, the projecting actuator member could be arranged to be capable of projecting right through the apparatus at both ends, whereby much greater variation in sampling depth could be achieved. By defining the sampling depth with reference to the bottom of the tank, or the sea bed, rather than by measurement from the suspension wire, significantly greater accuracy can be achieved. Moreover, by sampling with liquid inlets to the apparatus at the defined sampling height, the disadvantages of prior apparatus in which the liquid inlet is positioned at the bottom of the apparatus and thereby tends to become blocked with sludge, are avoided. The diameter of the liquid inlet drillings is relatively small so that liquid is sampled at a precisely defined level. The range of inlet aperture widths or diameters may be from 3.0 to 10.0 millimetres, depending on the liquid viscosity.

The inlet valve of the sampling apparatus could be actuated by tension means, for example a wire, cable or the like. Preferably, the arrangement would be such that actuation and support for the apparatus would be effected by a single wire or the like.

In the embodiment, the small overall diameter of the sampling apparatus permits it to be inserted through and used via an MMC stand having a top inlet diameter of 43 millimeters. Previously proposed apparatus is incapable of operating through the small inlet opening of the MMC stand's vapour lock O-ring.

In a further modification of the described embodiment, apertures are provided in the bottom plate or foot of the valve actuating member 132, so as to reduce the upthrust of the liquid thereon during descent through the liquid, in a tank being sampled. In this modification, and indeed in the described embodiment, the plate is able to retract right up against the bottom of the apparatus so as to permit liquid sampling very close to or at the bottom of the tank in certain conditions where this is desirable.

Figure 13:
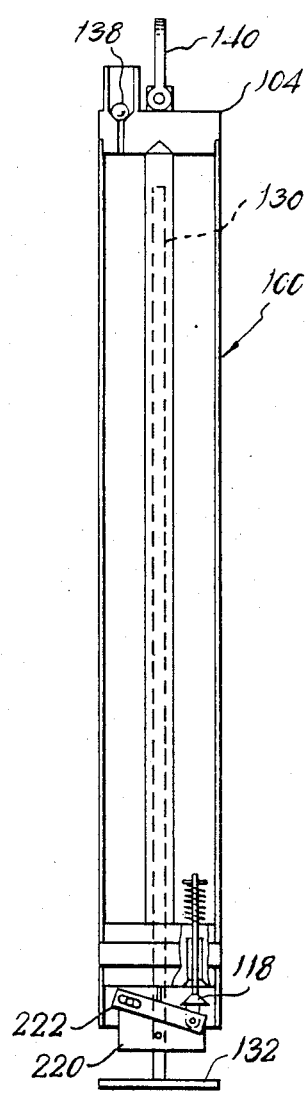

FIGS. 7 to 13 show a second embodiment of the invention. In this embodiment, parts corresponding to those in FIGS. 1 to 6 are given the same reference numerals and, in general, require no further discussion.

Attention is directed particularly to the structure and arrangement of the inlet valve assembly 200 which controls the inlet of fluid to sampling chamber 116 through a port 201. The valve member 118 itself is mounted on a rod or stem 202 actuated by a coiled compression spring 122, as in the previous embodiment. The conical valve member is adapted to seal against a seat 204 formed in an inlet member 206. Inlet member 206 has threaded portions 208 and 210 whereby it is screw-threadedly secured to main tube 102 and to a collar 212 respectively—these latter two components being formed with internal screw threads for the purpose. O-rings 214,216 seal the inlet member 206 to tube 102 and collar 212. O-ring 216 avoids the escape of air trapped in collar 212 during descent of the apparatus into a tank or the like, thereby ensuring that the entry of liquid into collar 212 as the apparatus descends through a body of liquid during use, is minimised until the valve assembly is opened, under operator control.

In this embodiment, the tube 128 mounted within main tube 102 forms a zone open at its outer end to the external body of liquid to be sampled, and which is sealed to member 206 against the escape into it of fluid within the sampling chamber 116. Valve actuating member 132 is telescopically received in tube 128 in an adjustable manner as described below. The top end of tube 128 is located in a recess formed in top cap 104, quite close to the port therein controlled by ball valve 138.

For actuating valve 118 there is provided an actuating mechanism 218 comprising an actuating block 220, a lever 222 and a pivot pin 224. Actuating block 220 is position-adjustably connectible to rod 130 in a manner to be described. Lever 222 is connected to block 220 by means of a pin projecting from the block and received in an elongated slot 226 at one end of the lever. At its other end, lever 222 is pivotally connected to a rod 228 projecting from valve member 118. Intermediate its ends, lever 222 is formed with a recess 230 to receive pin 224. It will now be seen that inward (upward as seen in FIG. 7) movement of rod 130 with respect to tube 102 causes clockwise angular movement of lever 222 about the end of pin 224, between the positions shown in FIGS. 12 and 13. This causes valve 118,204 to be opened.

FIG. 11 shows a finger-actuated adjustor mechanism for connecting block 220 to rod 130. A slidable U-shaped detent 232 is urged by a spring 234 to the position shown in FIG. 11. The user can adjust block 220 with respect to rod 130 by pressing on the end 236 of detent 232 so as to disengage the other end of the detent from the relevant hole 134 in rod 130. The detent can then be re-engaged with the rod at a new chosen position.

Attention is also directed to the holes or apertures 238 in base plate 132 for reducing upthrust during descent through a liquid. Note also that collar 212 is open at its lower end, whereby there is free access of liquid to valve mechanism 118,204. The collar serves to protect the valve actuating mechanism 218. For thick liquids, or other liquids not requiring screening, this arrangement provides improved access to the apparatus. The fill time for the apparatus may be reduced to about ten seconds.

In use, the apparatus functions very much as described above for the first embodiment. The valve actuating arrangements and the relatively small diameter of the valve 118 (0.5 to 1.0 centimeters) ensures easy opening of the valve when base plate 132 reaches the bottom. There is no need to bump the apparatus on the bottom. The valve spring and actuation mechanism is such that the valve opens under a weight of approximately one kilogram in air. The total weight of the apparatus when containing air only, is approximately two kilograms in water. The apparatus can be used at depths of the order of 100 meters, or indeed any depth such that the operator is able to sense and control the step of causing the apparatus to reach the bottom and to open its valve under its own weight.

In this embodiment, the simple mechanical actuation of the valves ensures complete safety for use, for example, in sampling highly volatile fuels. The valve and sealing arrangements maximise the sampling efficiency and accuracy. The independent actuation of the valves permits efficient valve actuation without the precision hitherto required by prior art apparatus employing linked valves. The outward opening of the valve members ensures efficient sealing during descent.

What is claim is:
1. Liquid sampling apparatus comprising:
 (a) a sealable sampling vessel having an upper end and a lower end and defining a sampling chamber to receive and temporarily store a liquid to be sampled, said liquid constituting a liquid in a liquid tank having a bottom surface or other tank structure therein, or constituting sea water overlying a sea bed;
 (b) support means for said sampling vessel whereby said sampling vessel can be lowered into the liquid to be sampled prior to sampling and subsequently raised after sampling when containing a sample of the liquid to be sampled;
 (c) the weight of said sampling vessel being such that when said chamber is full of air prior to sampling and the vessel is lowered into the liquid to be sampled, the vessel sinks;
 (d) an upper port formed in said sampling vessel at the upper end thereof to permit escape of air form within said chamber during the sampling process, and upper valve means mounted at said port to control the passage of fluids through said upper port;
 (e) a lower port formed in said sampling vessel at the lower end thereof to permit the entry into said chamber of liquid to be sampled during the sampling process, and lower valve means mounted at said port to control the passage of fluids through said lower port;
 (f) valve control means to permit control of said lower valve means to enable selective admission of the liquid, into which said apparatus is lowered, to sampled;
 (g) both said upper and lower valve means comprising valve members mounted for movement outwards and inwards with respect to said sampling vessel, respectively to open said valve means upon outward movement and to close said valve means upon inward movement;
 (h) said control means including a valve actuating assembly having a reversible lever mechanism, and an outwardly projecting actuator member extending below the lower end of said sampling vessel and engageable with said bottom surface or other structure, or said sea bed, said actuator member being mounted for movement outwards and inwards with respect to said sampling vessel and an operation connection connecting to the lower valve member to said reversible lever mechanism for actuating said lower valve member whereby, respectively, inward movement of said actuator member with respect to said sampling vessel causes outward movement of said lower valve member to open said lower valve means, and outward movement of said actuator member with respect to said sampling vessel causes inward movement of said lower valve member to close said lower valve means;
 (i) said lower valve means comprising said lower valve member, a cooperating valve seat, a valve guide for said valve member, and spring means biasing said valve member in inward and closing direction to close the lower valve means automatically upon raising of the apparatus from said bottom surface or other structure or said sea bed;

(j) said operative connection of said actuator member to said lower valve member being adjustable for permitting the degree of projection of said actuator member to be adjusted to vary the depth of said sampling vessel with respect to said bottom surface or other structure or said sea bed at which said lower valve means is opened;

(k) said actuator member including a stem and said operative connection of said actuator member to said lower valve means comprising said valve actuating assembly, said stem of said actuator member being slidingly received in said being lengthwise-adjustable with respect to said valve actuating assembly by means of a releasable detent mechanism; and (l) said stem being telescopically received in tube means having a lower outer end and extending lengthwise into said sampling chamber and forming a zone open at its lower outer end to the main body of the liquid to be sampled and sealed against the escape into said zone of fluid in the sampling chamber.

2. Apparatus of claim 1 including a plate at the outer end of said projecting actuator member for engagement with said bottom surface or other structure of said sea bed, said plate being formed with apertures to reduce the upthrust thereon during descent into the liquid.

3. Apparatus of claim 2 wherein said plate is in the form of a transversely extending foot plate constituting stabilizing support means facilitating the apparatus to stand upright on the bottom of a liquid tank during sampling.

4. Apparatus of claim 1 wherein said sampling vessel is provided at its lower end with a removable end fitting, and said tube means is mounted on said removable end fitting.

5. Apparatus of claim 4 wherein said removable end fitting has an outer side and said lever mechanism is mounted at said outer side.

6. Liquid sampling apparatus comprising:
a sealable longitudinal sampling vessel having an upper end and a lower end and defining an internal sampling chamber to receive and temporarily store a liquid to be sampled, said liquid constituting a body of liquid overlying a submerged bottom surface downwardly engageable by engagement means at the lower end of said vessel;

support means for lowering said vessel into said liquid prior to sampling and for raising the vessel after sampling when containing a sample of said liquid, the vessel weight being sufficient for the vessel to sink in the liquid when said chamber is full of air prior to sampling and the vessel is lowered into the liquid;

an upper port formed at the vessel upper end to permit escape of air from within said chamber during the sampling process, and a pressure responsive upper valve mounted at said upper port to control the passage of fluids through said upper port, including an upper valve member mounted for movement outwards relative to said vessel to open said upper valve under excess internal pressure in said chamber relative to the existing pressure of the liquid external to said vessel when the vessel has been lowered into the liquid, and correspondingly for movement inwards relative to said vessel to close said upper valve automatically in the absence of excess internal pressure in said chamber relative to the existing pressure of the liquid external to said vessel when the vessel has been lowered into the liquid;

a lower port formed at the vessel lower end to permit entry into said chamber of liquid to be sampled during the sampling process, and a mechanically actuated lower valve mounted at said lower port to control the passage of fluids through said port, including a lower valve member having a biasing spring and mounted for movement outwards relative to said vessel to open said lower valve against the force of the biasing spring and the existing pressure of the liquid external to said vessel when the vessel has been lowered into the liquid, and correspondingly for movement inwards relative to said vessel to close said lower valve automatically under the force of the biasing spring and the existing pressure of the liquid external to said vessel when the vessel has been lowered into the liquid;

the upper valve member and lower valve member being movable independently of each other, and the lower valve being disposed completely within said vessel and spaced from the upper end thereof; and an actuating mechanism for moving the lower valve member to open the lower valve, including an operatively mounted lever having one end operatively connected to the lower valve member and an opposite end operatively connected to a longitudinally movable control member, a longitudinally movable elongate actuator member, and adjustable connection means for adjustably connecting the actuator member to the control member;

said control member being mounted at the lower end of said vessel for longitudinal movement outwards relative to said vessel to cause said lever to move said lower valve member inwards to close said lower valve, and correspondingly for longitudinal movement inwards relative to said vessel to cause said lever to move said lower valve member outwards to open said lower valve;

said lower portion engagement means extending below the vessel lower end for engagement with such bottom surface, and said actuator member having longitudinally inserted upper portion extending inwardly into the vessel; and said adjustable connection means connecting the actuator member to the control member at a selective longitudinal position of movement of the actuator member relative to said vessel for common movement of the actuator member and the control member, said selective longitudinal position of movement determining the degree of projection of the lower portion of the actuator member below the vessel lower end for varying the depth of said vessel relative to said bottom surface, whereby upon engagement of the lower portion of the actuator member with said bottom surface, the vessel weight will cause the lever to move relative to said actuator member and control member to open said lower valve to permit entry into said chamber of liquid to be sampled, and in turn the incoming liquid will upwardly displace and compress the air in said chamber to cause the upper valve to open under the thereby generated excess internal pressure in said chamber for escape of such air and completion of the filling of the chamber with the liquid to be sampled, after which the upper valve will reclose automatically, and upon raising the vessel the lever will move relative to said actuator member and control member to reclose the lower valve automatically.

7. Apparatus of claim 6 wherein the vessel is provided with an internal elongate tube having a lower outer end at the lower end of the vessel open to the liquid external to the vessel and closed off from entry thereinto of fluid in said chamber, and the actuator member comprises a rod having an upper portion slidably received in and lengthwise adjustable relative to the control member and telescopically received in the tube.

* * * * *

UNITED STATES PATENT AND TRADEMARK OFFICE
CERTIFICATE OF CORRECTION

PATENT NO. : 4,790,197
DATED : December 13, 1988
INVENTOR(S) : Riginos Kimonides It is certified that error appears in the above-identified patent and that said Letters Patent is hereby corrected as shown below:

Claim 1, Col. 6, line 22, delete "form" and substitute therefor --from--; line 35, after "to" insert --be--; line 51, delete "operation" and substitute therefor --operative--.

Claim 6, Col. 8, line 42, delete "lower portion".

Signed and Sealed this

Twenty-third Day of May, 1989

Attest:

DONALD J. QUIGG

Attesting Officer

Commissioner of Patents and Trademarks